(12) United States Patent
Ding et al.

(10) Patent No.: US 10,676,478 B2
(45) Date of Patent: *Jun. 9, 2020

(54) 7-(THIAZOL-5-YL) PYRROLOPYRIMIDINE COMPOUND AS TLR7 AGONIST

(71) Applicant: CHIA TAI TIANQING PHARMACEUTICAL GROUP CO., LTD., Lianyungang (CN)

(72) Inventors: Zhaozhong Ding, Shanghai (CN); Fei Sun, Shanghai (CN); Lifang Wu, Shanghai (CN); Hao Wu, Shanghai (CN); Shuhui Chen, Shanghai (CN); Ling Yang, Jiangsu (CN)

(73) Assignee: CHIA TAI TIANQING PHARMACEUTICAL GROUP CO., LTD., Lianyungang, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/772,995

(22) PCT Filed: Nov. 4, 2016

(86) PCT No.: PCT/CN2016/104644
§ 371 (c)(1),
(2) Date: May 2, 2018

(87) PCT Pub. No.: WO2017/076346
PCT Pub. Date: May 11, 2017

(65) Prior Publication Data
US 2018/0370976 A1 Dec. 27, 2018

(30) Foreign Application Priority Data
Nov. 5, 2015 (CN) .......................... 2015 1 0744651

(51) Int. Cl.
| C07D 487/04 | (2006.01) |
| C07D 277/20 | (2006.01) |
| A61K 31/519 | (2006.01) |
| A61P 31/12 | (2006.01) |
| A61P 31/14 | (2006.01) |
| A61P 31/20 | (2006.01) |

(52) U.S. Cl.
CPC .......... *C07D 487/04* (2013.01); *A61K 31/519* (2013.01); *A61P 31/12* (2018.01); *A61P 31/14* (2018.01); *A61P 31/20* (2018.01); *C07D 277/20* (2013.01)

(58) Field of Classification Search
CPC .. C07D 487/04; C07D 277/20; A61K 31/519; A61P 31/12; A61P 31/14
USPC ...................... 544/280; 514/265.1
See application file for complete search history.

(56) References Cited

U.S. PATENT DOCUMENTS

| 9,962,388 B2 * | 5/2018 | Ding .................... A61K 31/519 |
| 2010/0143301 A1 | 6/2010 | Desai et al. |
| 2015/0266883 A1 | 9/2015 | Coe et al. |
| 2015/0284396 A1 | 10/2015 | Coe et al. |

FOREIGN PATENT DOCUMENTS

| CL | 201501342 | 10/2015 |
| CL | 201700379 | 9/2017 |
| CL | 201801171 | 5/2018 |
| CL | 201801210 | 5/2018 |
| CL | 201801216 | 5/2018 |
| CN | 104780922 | 7/2015 |
| CN | 104780924 | 7/2015 |
| CN | 105367576 | 3/2016 |
| EP | 3 190 113 A1 | 7/2017 |
| WO | WO-2007/024707 A2 | 3/2007 |
| WO | WO-2014/081644 A1 | 5/2014 |
| WO | WO-2014/081645 A1 | 5/2014 |

OTHER PUBLICATIONS

Ohto etal., Microbes and Infection 16 (2014) 273-282.*
Yu etal., Biochimica et Biophysica Acta 1835(2013) 144-154.*
Zhao etal., Frontiers in Immunology. 5, 1-6,2014.*
International Search Report and Written Opinion for PCT/CN2016/104644 dated Nov. 11, 2015, with English translation.
Australian First Examination Report, issued in Australian Patent Application No. 2016349080 (dated Nov. 5, 2018).
Eurasian Official Action, issued in Eurasian Application No. 201894099 (dated Jan. 22, 2019).
Greene, et al., "Protective Groups in Organic Synthesis", 2nd Ed., pp. 362-385 (1991).
Lanford, et al., "GS-9620, an Oral Agonist of Toll-Like Receptor-7, Induces Prolonged Suppression of Hepatitis B Virus in Chronically Infected Chimpanzees", Gastroenterology 144: 1508-1517 (2013).
Maehr, "A Proposed New Convention for Graphic Presentation of Molecular Geometry and Topography", Journal of Chemical Education 62(2): 114-120 (1985).

(Continued)

*Primary Examiner* — Venkataraman Balasubramanian
(74) *Attorney, Agent, or Firm* — Foley & Lardner LLP (57) ABSTRACT

The present invention relates to a 7-(thiazol-5-yl)pyrrolopyrimidine compound as a TLR7 agonist, and particularly relates to a compound shown in formula (I), pharmaceutically acceptable salt and preparation method thereof, a pharmaceutical composition containing such a compound, and usage thereof in preparing an antiviral drug.

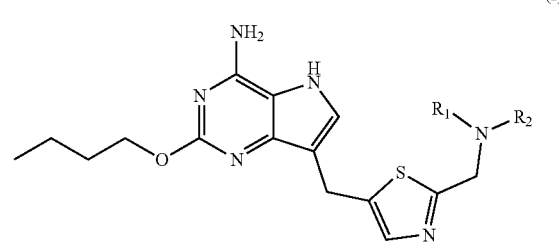

(I)

11 Claims, 2 Drawing Sheets

(56) References Cited

OTHER PUBLICATIONS

New Zealand First Examination Report, issued in New Zealand Application No. 742453 (dated Aug. 6, 2018).
Remington, The Science and Practice of Pharmacy, 21st Ed., Ch. 39-42, 89 pages (2005).
Sauder, "Imiguimod: modes of action", British Journal of Dermatology 149(Suppl. 66): 5-8 (2003).
Wu, et al., "Resiquimod: a new immune response modifier with potential as a vaccine adjuvant for Th1 immune responses", Antiviral Research 64: 79-83 (2004).
Canadian Office Action, issued in Canadian Patent Appln. No. 3,004,173, 4 pages (dated Apr. 17, 2019).
Chinese Office Action, issued in Chinese Patent Appln. No. 201680064165.2, 8 pages (dated May 5, 2019).
European Extended Search Report, issued in European Patent Appln. No. 16861614.2, 8 pages (dated Mar. 1, 2019).
Chilean Office Action, issued in Chilean Pat. App. No. 201801207, 18 pages (dated Aug. 21, 2019).
Eurasian Office Action, issued in Eurasian Pat. App. No. 201891099/28, 2 pages (dated Aug. 5, 2019).
Indian Office Action, issued in Indian Pat. App. No. 201817019356, 5 pages (dated Jul. 30, 2019).
Israeli Preliminary Office Action, issued in Israeli Pat. App. No. 259115, 3 pages (dated Sep. 2, 2019).

\* cited by examiner

7-(THIAZOL-5-YL) PYRROLOPYRIMIDINE COMPOUND AS TLR7 AGONIST

This application is a U.S. National Stage of International Application No. PCT/CN2016/104644, filed on Nov. 4, 2016, designating the United States, and claiming the benefit of Chinese Patent Application No. 201510744651.6, filed with the Chinese Patent Office on Nov. 5, 2015, both of which are hereby incorporated by reference in their entireties.

TECHNICAL FIELD

Provided is a 7-(thiazol-5-yl)pyrrolopyrimidine cyclic compound or a pharmaceutically acceptable salt thereof as TLR7 agonist, which is useful for treating or preventing viral infection, particularly hepatitis B or hepatitis C viral infection.

BACKGROUND

Toll-like receptor is expressed by various immune cells and recognizes high reserved structural motifs: Pathogen Associated Molecular Pattern (PAMP) expressed by microorganism pathogens or Damage Associated Molecular Patterns (DAMP) released by dead cells. PAMP or DAMP stimulates Toll-like receptor to trigger signal cascade which induces the activations of transcriptional factors like AP-1, NF-κB and interferon regulators (pulse response function). It results in various cell responses, including productions of interferons, proinflammatory cytokines and effector cytokines, whereby immune response is produced.

By far, 13 types of Toll-like receptors have been discovered in mammal. Toll-like receptors 1, 2, 4, 5 and 6 are mainly expressed on the cell surface while Toll-like receptors 3, 7, 8 and 9 are expressed in the endosome. Different Toll-like receptors recognize ligands derived from different pathogens. Toll-like receptor 7 (TLR7) is expressed and ligand recognized by plasmaeytoid dendritic cells (pDC) to induce the secretion of interferon α (IFN-α). Toll-like receptor 7 (TLR7) and Toll-like receptor 8 (TLR8) are highly homologous and therefore the ligand of TLR7 in many cases is also that of TLR8. TLR8 stimulation mainly induces the productions of cytokines like tumor necrosis factor α (TNF-α) and chemoattractant. Interferon α is one of the main medicines for treating chronic hepatitis B or hepatitis C while TNF-α is a proinflammatory cytokine, of which the over secretion will result severe side effects.

There have been reported several TLR7 agonists, like Imiquimod (British Journal of Dermatology 2003; 149 (Suppl. 66): 5-8), Resiquimod (Antiviral Research 64 (2004) 79-83), GS-9620 (Gastroenterology (2013), 144(7), 1508-1517). Nevertheless, it is desirable to have novel TLR7 agonists with better selectivity, activity and safety.

SUMMARY

In an aspect, provided is a compound of formula (I) or a pharmaceutically acceptable salt thereof, wherein
$R_1$ and $R_2$ are each independently selected from the group consisting of H and $C_{1-4}$alkyl, or
$R_1$ and $R_2$ together with the N atom to which they are attached form a 4-8 membered heterocycloalkyl, the 4-8 membered heterocycloalkyl is optionally substituted with one or more $R_3$, $R_3$ is each independently selected from the group consisting of hydroxyl, halogen, cyano, $C_{1-4}$alkyl and $C_{1-4}$alkoxy.

In an embodiment, the 4-8 membered heterocycloalkyl may contain 0, 1, 2 or 3 additional heteroatoms selected from the group consisting of N, O and S.

In another embodiment, the 4-8 membered heterocycloalkyl may be 4 membered, 5 membered, 6 membered, 7 membered or 8 membered heterocycloalkyl.

In another embodiment, $R_3$ is independently selected from the group consisting of hydroxyl, F, Cl, Br, CN, methyl, ethyl, propyl, methoxyl, ethoxyl and propoxy.

In a specific embodiment, the group formed by $R_1$, $R_2$ together with the N atom to which they are attached is selected from the group consisting of:

In some embodiment, the compound of formula (I) is the following compound:

In another aspect, provided is a pharmaceutical composition, comprising a compound of formula (I) and/or a pharmaceutically acceptable salt thereof, and one or more pharmaceutically acceptable carriers and/or excipients. The pharmaceutical composition may further optionally comprise one or more additional therapeutical agents.

In another aspect, provided is a method for treating or preventing viral infection, comprising administering to a subject in need thereof a compound of formula (I) or a pharmaceutically acceptable salt thereof, or the pharmaceutical composition according to the invention in therapeutically or prophylactically effective amount.

In a further aspect, provided is use of a compound of formula (I) or a pharmaceutically acceptable salt thereof, or the pharmaceutical composition according to the invention for the manufacture of a medicament for treating or preventing viral infection.

In a yet aspect, provided is a compound of formula (I) or a pharmaceutically acceptable salt thereof, or the pharmaceutical composition according to the invention for use in treating or preventing viral infection.

In some embodiments according to the invention, the viral infection is viral infection of dengue fever virus, yellow fever virus, west nile virus, Japanese encephalitis virus, tick borne encephalitis virus, Kunjin virus, Murray Valley encephalitis virus, St Louis encephalitis virus, Omsk Hemorrhagic Fever virus, bovine viral diarrhea virus, Zika virus, or hepatitis virus. In a preferable embodiment, the viral infection is hepatitis viral infection. In a further preferable embodiment, the viral infection is hepatitis B or hepatitis C viral infection.

DETAILED DESCRIPTION

General Definition and Terms

Unless stated otherwise, the terms and phrases used herein have the following meaning. A specific term or phrase shall not be considered as unclear or indefinite when it is not specifically defined. It should be understood according to the general meaning The trade name used herein refers to the corresponding product or the active ingredient.

When used with a numerical variable, the term "approximate" or "about" usually refers to the value of the variable and all the values of the variable within the experimental error (for example, within an average 95% confidence interval) or within ±10% of the specified value, or a wider range.

The expression "comprise" or its synonyms "contain", "include", "have" or the like is open-ended, which does not exclude other unlisted elements, steps or ingredients. The expression "consist of" excludes any unlisted elements, steps or ingredients. The expression "substantially consist of" refers to specified elements, steps or ingredients within a given range, together with optional elements, steps or components which do not substantively affect the basic and novel feature of the claimed subject matter. It should be understood that the expression "comprise" encompasses the expressions "substantially consist of" and "consist of".

The term "optional" or "optionally" means the event described subsequent thereto may or may not happen. This term encompasses the cases that the event may or may not happen. For example, the expression that ethyl is "optionally" substituted with halogen means that the ethyl is unsubstituted ($CH_2CH_3$), mono-substituted (eg. $CH_2CH_2F$), multi-substituted (e.g. $CHFCH_2F$, $CH_2CHF_2$ etc.), or is completely substituted ($CF_2CF_3$). It should be noted for a person skilled in the art that, for any group containing one or more substituents, a substitution or substitution mode which does not possibly exist in space and/or cannot be synthesized will not be introduced.

The term $C_{m-n}$ used herein means that the moiety has m-n carbon atoms. For example, "$C_{1-4}$alkyl" means said alkyl has 1-4 carbon atoms.

The numerical range herein refers to each of the integers therein and subranges constituted by the integers. For example, "$C_{1-4}$" means said group may have 1 carbon atom, 2 carbon atoms, 3 carbon atoms or 4 carbon atoms. Accordingly, "$C_{1-4}$alkyl" encompasses "$C_{2-3}$alkyl", "$C_{1-3}$alkyl", "$C_{2-4}$alkyl" as well as $C_1$alkyl, $C_2$alkyl, $C_1$alkyl, $C_1$alkyl or the like.

The term "substituted" means any one or more hydrogen atoms on a given atom are replaced by substituent(s), provided that the valence of the given atom is normal and the compound after substitution is stable.

When any variable (e.g. R) occurs at the composition or structure of the compound over one time, it is defined independently at each case. Therefore, for example, if a group is substituted by 0-2 R, the group may be optionally substituted by at most two R and R has independent option at each case. Additionally, a combination of substituents and/or the variants thereof are allowed only if such a combination will result in a stable compound.

Unless stated otherwise, the term "hetero" means heteroatom or heteroatom radical (i.e. a radical containing heteroatom), i.e. the atoms beyond carbon and hydrogen atoms or the radical containing such atoms. Preferably, the heteroatom is independently selected from the group consisting of O, N, S and the like. In an embodiment wherein two or more heteroatoms are involved, the two or more heteroatoms may be the same, or part or all of the two or more heteroatoms may be different.

The term "halo" or "halogen" refers to F, Cl, Br or I.
The term "hydroxyl" refers to —OH group.
The term "cyano" refers to —CN group.
The term "alkyl" refers to a linear or branched saturated aliphatic hydrocarbyl group composed of carbon and hydrogen atoms, which is linked to rest of the molecule via a single bond. Non-limiting examples of $C_{1-4}$alkyl comprise but not limited to methyl, ethyl, propyl, isopropyl, n-butyl, isobutyl, sec-butyl and tert-butyl.

The term "$C_{1-4}$alkoxy" refers to "$C_{1-4}$ alkyl", which is connected to the rest of the molecule via "—O—", wherein the "$C_{1-4}$ alkyl" is defined as above.

The term "heterocycloalkyl" refers to a saturated monocyclic or polycyclic system group, wherein part of the ring atoms are heteroatoms selected from the group consisting of N, O, S, and rest of the ring atoms are C. Accordingly, the term "4-8 membered heterocycloalkyl" refers to the heterocycloalkyl containing 4-8 ring atoms in the system, wherein one or more ring atoms are heteroatoms selected from the group consisting of N, O, S. The examples of 4 membered heterocyclohydrocarbyl comprise but not limited to azetidinyl. The examples of 5 membered heterocycloalkyl comprise but not limited to pyrrolidinyl, isoxazolidinyl, oxazolidinyl, isothiazolidinyl, thiazolidinyl, imidazolidinyl. The examples of 6 membered heterocyclohydrocarbyl comprise but not limited to piperidinyl, morpholinyl, piperazinyl. The examples of membered heterocyclohydrocarbyl comprise but not limited to azacycloheptanyl, oxaazabicyclo[2.2.1]heptyl, or the like.

The term "pharmaceutically acceptable" refers to the compound, material, composition and/or dosage form, which are within the scope of reliable medical judgment, suitable for contact with human and animal tissues, without over toxicity, irritation, allergic reaction or other problems or complications and has acceptable benefit/risk ratio.

The term "pharmaceutical composition" refers to an active compound (e.g. a compound of formula (I) or a pharmaceutically acceptable salt thereof), which is optionally combined with one or more pharmaceutically acceptable chemical components (for example, but not limited to carrier and/or excipient).

The term "pharmaceutically acceptable carrier" refers to those carriers which have no significant irritation and do not impair the bioactivity and property of the active compound. The "pharmaceutically acceptable carrier" refers to inert substance which is administered together with active ingredient and is beneficial to the administration thereof, and comprises but not limited to any of the following substances approved by State Food and Drug Administration for use in human or animal (e g livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference. The term "excipient" generally refers to the vehicle, diluent and/or medium used to formulate effective pharmaceutical composition.

The term "administration" or "administrating" or the like refers to a method that enables a compound or composition to be delivered to a desired site of biological action. Such methods comprise but not limited to oral, parenteral (including intravenous, subcutaneous, intraperitoneal, intramuscular, intravascular injection or infusion), local, rectal administration or the like.

As for pharmaceutical or pharmacological active agent, the term "effective amount", "therapeutically effective amount" or "prophylactically effective amount" refers to the amount of the medicament or agent which is not toxic but sufficient to achieve the desired effect. With respect to the oral formulation herein, the "effective amount" for an active substance in the composition refers to the amount required to achieve the desired effect in combination with another active substance in the composition. The effective amount may be determined individually and depends on the age and general condition of the receptor as well as specific active substance. The effective amount in specific case can be determined by a person skilled in the art through conventional test.

The term "active ingredient", "therapeutic agent", "active substance" or "active agent" refers to a chemical entity useful for treating or preventing target disorder, disease or condition effectively.

"Protecting group" refers to a type of substituent that is employed to block or protect a certain functionality while reacting with other functional groups on the compound. For example, an "amino-protecting group" is a substituent attached to an amino group that blocks or protects the amino functionality in the compound. Suitable amino-protecting groups include but are not limited to acetyl, trifluoro group, t-butoxycarbonyl (BOC), benzyloxycarbonyl (CBZ), 9-fluorenylmethyl chloroformate (Fmoc), 2-(trimethylsilyl) ethoxyl methyl (SEM) and the like. General description of protecting groups and their use can be found in Greene and Wuts, Protective Groups In Organic Synthesis, Wiley and Sons, 1991.

Compound According to the Invention

Provided is a compound of formula (I) or a pharmaceutically acceptable salt thereof,

(I)

wherein each of the groups is defined as above.

The expression "the group formed by $R_1$, $R_2$ together with the N atom to which they are attached" refers to the group formed by moiety in the compound of formula (I). The examples comprise but not limited to The additional heteroatom(s) in the expression "the 4-8 membered heterocycloalkyl may contain 0, 1, 2 or 3 additional heteroatoms selected from the group consisting of N, O and S" refers to heteroatom(s) other than the N atom in moiety. Preferably, the additional heteroatom may be selected from the group consisting of N, O and S, and the number may be 0, 1, 2 or 3.

In a preferable embodiment, provided is the compound of the following formula:

It should be understood that the compound according to the invention may be present in the form of pharmaceutically acceptable salt. As pharmaceutically acceptable salt, for example, the following examples may be mentioned: metal salts, ammonium salts, salts formed with organic bases, inorganic acids, organic acids, basic or acidic amino acids or the like. Non-limiting examples of metal salts comprise but not limited to salts of alkaline metals, for example sodium salt, potassium salt or the like; salts of alkaline earth metals, for example calcium salt, magnesium salt, barium salt or the like; aluminum salt or the like. Non-limiting examples of the salts formed with organic bases comprise but not limited to those formed with trimethylamine, triethylamine, pyridine, methylpyridine, 2,6-dimethylpyridine, ethanolamine, diethanolamine, triethanolamine, cyclohexylamine, dicyclohexylamine or the like. Non-limiting examples of the salts formed with inorganic acids comprise but not limited to those formed with hydrochloric acid, hydrobromic acid, nitric acid, sulphuric acid, phosphoric acid or the like. Non-limiting examples of the salts formed with organic acids comprise but not limited to those formed with formic acid, acetic acid, trifluoroacetic acid, fumaric acid, oxalic acid, malic acid, maleic acid, tartaric acid, citric acid, succinic acid, methanesulfonic acid, benzene sulfonic acid, p-toluenesulfonic acid or the like. Non-limiting examples of the salts formed with basic amino acids comprise but not limited to those formed with arginine, lysine, ornithine or the like. Non-limiting examples of the salts formed with acidic amino acids comprise but not limited to those formed with aspartic acid, glutamic acid or the like.

The pharmaceutically acceptable salts according to the invention may be prepared from the parent compound containing acidic or basic group through conventional chemical procedures. Generally, such salts may be prepared through the reaction of the compounds in the form of free acid or base with stoichiometric appropriate base or acid in water, organic solvent or the mixture thereof. Typically, nonaqueous medium like ether, ethyl acetate, ethanol, isopropanol or acetonitrile etc. are preferable.

The compound according to the invention may have one or more stereoisomeric centers and each of the centers may exist in R configuration or S configuration or combination thereof. Therefore, the compounds according to the invention comprise all the individual configurational stereoisomeric forms, position isomeric forms, diastereomeric forms, enantiomeric forms and epimeric forms as well as their corresponding mixtures. The technology to reverse a particular stereoisomeric center or keep it unchanged as well as the technology of stereoisomers mixtures resolution is well-known in the art and a person skilled in the art can select particular procedure according to particular requirements.

The compounds according to the invention may exist in unsolvated or solvated forms, including hydrate form. In general, the solvated forms are equivalent to unsolvated forms and both of them are encompassed within the scope of the invention. The compounds according to the invention may exist in polymorphic or amorphous forms and such forms are encompassed within the scope of the invention.

The compound according to the invention may contain atomic isotope in non-natural ratio at one or more atoms constituting said compound. For example, the compound may be labeled with radioisotope, such as Tritium ($^3$H), Iodine-125($^{125}$I) or C-14($^{14}$C). Alternation of all the radioisotopes of the compound, either radioactive or not, is encompassed within the scope of the invention.

The present invention also encompasses any pharmaceutically acceptable derivative of the compounds according to formula (I), e.g. ester, salt of the ester. A particularly preferable derivative is prodrug. Upon administration to a subject, such a derivative can directly or indirectly provide the compound according to the invention or its metabolite or residue with pharmaceutical activity. A particularly preferable derivative (e.g. prodrug) is the compound, which upon administration to a subject, will increase bioavailability of the compound according to the invention or improve delivery of the parent compound to the tissues or organs of a living body.

Administration, Pharmaceutical Composition and Kit

Provided is a method for treating or preventing viral infection, comprising administering to a subject in need thereof a compound of formula (I) or a pharmaceutically acceptable salt thereof, or the pharmaceutical composition according to the invention in therapeutically or prophylactically effective amount. The method may optionally comprise administering one or more additional active agents for treating or preventing the viral infection.

Alternatively, provided is use of a compound of formula (I) or a pharmaceutically acceptable salt thereof, or the pharmaceutical composition according to the invention for the manufacture of a medicament for treating or preventing viral infection. In a particular embodiment, the compound of formula (I) or the pharmaceutically acceptable salt thereof may be used in combination with one or more additional active agents for treating or preventing the viral infection.

Alternatively, provided is a compound of formula (I) or a pharmaceutically acceptable salt thereof, or the pharmaceutical composition according to the invention for use in treating or preventing viral infection. In a particular embodiment, the compound of formula (I) or the pharmaceutically acceptable salt thereof may be used in combination with one or more additional active agents for treating or preventing the viral infection.

In some embodiments according to the invention, the viral infection is viral infection of dengue fever virus, yellow fever virus, west nile virus, Japanese encephalitis virus, tick borne encephalitis virus, Kunjin virus, Murray Valley encephalitis virus, St Louis encephalitis virus, Omsk Hemorrhagic Fever virus, bovine viral diarrhea virus, Zika virus, or hepatitis virus. In a preferable embodiment, the viral infection is hepatitis viral infection, particularly hepatitis B or hepatitis C viral infection.

Provided is also a pharmaceutical composition, comprising a compound of formula (I) or a pharmaceutically acceptable salt thereof, and one or more pharmaceutically acceptable carriers and/or excipients. The pharmaceutical composition may further optionally comprise one or more additional active agents.

The pharmaceutical composition according to the invention may be prepared by combining the compound according to the invention or the salt thereof with a pharmaceutically acceptable carrier. For example, it may be formulated into solid, semi-solid, liquid or gas formulation, such as tablet, pill, capsule, powder, granule, ointment, emulsion, suspension, solution, suppository, injection, inhalant, gel, microsphere, aerosol or the like.

The pharmaceutical composition according to the invention may be prepared by the processes well-known in the art, such as conventional mixing, dissolution, granulation, dragee coating, levigation, emulsion, freeze-drying or the like.

Typical routes for administering the compound according to the invention or the pharmaceutically acceptable salt thereof or the stereoisomer thereof or the pharmaceutical composition thereof comprise but not limited to oral, rectal, transmucosal, enteral administration or local, transcutaneous, inhalant, parenteral, sublingual, intravaginal, intranasal, intraocular, intraperitoneal, intramuscular, subcutaneous, intravenous administration.

As for oral administration, the active compounds may be mixed with the pharmaceutically acceptable carriers well-known in the art to prepare the pharmaceutical composition. The carriers may be used to prepare the compounds according to the invention into tablet, pill, troche, dragee, capsule, liquid, gel, slurry, suspension or the like useful for oral administration to the patient.

Solid oral composition may be prepared by conventional mixing, filling or compressing processes, for example, by the following processes: mixing the active compounds with solid excipients, optionally milling the resultant mixture, adding other proper adjuvants if necessary, and then processing the mixture into granules so as to obtain the core of tablet or dragee. The proper adjuvants comprise but not limited to binder, diluent, disintegrant, lubricant, glidant, sweetener, corrigent or the like. Additional examples comprise microcrystalline cellulose, glucose solution, acacia gel, gelatine solution, sucrose and starch paste; talcum, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, maize starch, potato starch, methylcellulose, agar, carboxymethyl cellulose, crosslinked polyvinylpyrrolidone or the like. The core of dragee may be optionally coated through well-known processes in conventional pharmaceutical practice, especially by an enteric coating.

The pharmaceutical composition according to the invention may be useful for parenteral administration, for example as appropriate unit dosage form like sterile solution, suspension or freeze dried product. Proper excipients may be used, such as filler, buffer or surfactant.

The compound of formula (I) or the pharmaceutically acceptable salt thereof according to the invention may be administered by any suitable route and process, for example by oral or parenteral administration (e.g. intravenous administration). The therapeutically or prophylactically effective amount of the compound of formula (I) may range from about 0.0001 to 20 mg/Kg bodyweight/day, for example, 0.001 to 10 mg/Kg bodyweight/day.

The dosing frequency of the compound of formula (I) depends on requirements of the individual patient, for example one or two or more times per day. Administration may be intermittent, for example, during the period of several days, the patient receives the daily dosage of the compound of formula (I), and then during the period of several days or a longer time, the patient does not receive the daily dosage of the compound of formula (I).

Provided is also a pharmaceutical combination, e.g. a kit, which comprises a) a first active agent which is a compound as disclosed herein; b) one or more additional active agents. The pharmaceutical combination may comprise instructions for its administration if necessary. If necessary, the above a) and b) may be provided in the same container or different containers. The pharmaceutical combination may further comprise the agents for assisting administration in the same container or different containers, e.g. the pharmaceutically acceptable carriers and/or excipients as mentioned above. Optionally, the kit may comprise a unit for diagnosis of viral infection (for example, the above-mentioned viral infections).

Synthesis and Preparation

The compound according to the invention can be prepared through various synthesis processes well-known to a person skilled in the art, including the specific embodiments illustrated below, the embodiments through combination of such specific embodiments with other chemical synthesis processes as well as equivalents well-known to a person skilled in the art. The preferable embodiments comprise but not limited to the working Examples herein. The chemical reaction of the specific embodiment according to the invention may be performed in appropriate solvent which should be suitable for the chemical change and required reagent and material according to the invention. To obtain the compound according to the invention, a person skilled in the art sometimes needs to perform modification or selection to synthesis step or reaction procedure based on the known embodiments.

One important factor in designing any synthesis scheme in the art lies in selecting an appropriate protective group for reactive group (e g amino in the invention). A person skilled in the art may refer to Protective Groups In Organic Synthesis, Wiley and Sons, 1991 by Greene and Wuts. The above cited references above are incorporated herein by reference in entirety.

For example, the compound of general formula (I) according to the invention may be prepared by a person skilled in the field of organic synthesis with standard procedures according to the following scheme:

Preparation of compound of formula 4: compound of formula 1 as starting material is reacted with compound of formula 2 via condensation reaction to give compound of formula 3, which is used to give compound of formula 4 under the action of n-butyllithium and DMF.

Preparation of compound of formula (I): compound of formula 5, with the protection of SEM, is used to give compound of formula 6, which is subjected to amino substitution to give compound of formula 7; compound of formula 7 is reacted with n-butanol under the action of Na to give compound of formula 8, which is subjected to deprotection of SEM protective group under the action of TFA to give compound of formula 9; compound of formula 9 is reacted with compound of formula 4 to give compound of formula 10, which is subjected to removal of hydroxyl to give compound of formula (I).

The solvents used herein are commercially available and can be used without further purification. The reactions are generally performed under inert nitrogen in anhydrous solvent. Data of proton magnetic resonance is recoded in Bruker Avance III 400 (400 MHz) spectrometer, with the chemical shift shown as (ppm) at tetramethylsilane low field. Mass spectrometry is determined on Agilent 1200 plus 6110 (&1956A). LC/MS or Shimadzu MS includes a DAD: SPD-M20A (LC) and Shimadzu Micromass 2020 detector. Mass spectrometer is equipped with an electrospray ionization (ESI) operated at positive or negative mode.

The compounds are nominated manually or by the ChemDraw® software. The names of commercially available compounds provided in the catalog of the supplier are used.

High performance liquid chromatographic analysis is performed with Shimadzu LC20AB system equipped with Shimadzu SIL-20A auto-sampler and Japanese Shimadzu DAD: SPD-M20A detector on Xtimate C18 (3 m filler, 2.1×300 mm) chromatographic column. 0-60AB_6 min method: linear gradient is applied, wherein elution is initiated with 100% A (A is 0.0675% TFA aqueous solution) and terminated with 60% B (B is 0.0625% TFA in MeCN solution) (the whole process is 4.2 min), and then 60% B is used for elution for 1 min. The chromatographic column is further equilibrated for 0.8 min to reach 100:0 and the total operational time is 6 min. 10-80AB_6 min method: linear gradient is applied, wherein elution is initiated with 90% A (A is 0.0675% TFA aqueous solution) and terminated with 80% B (B is 0.0625% TFA in acetonitrile solution) (the whole process is 4.2 min), and then 80% B is used for elution for 1 min. The chromatographic column is further equilibrated for 0.8 min to reach 90:10 and the total operational time is 6 min. The column temperature is 50° C. and velocity is 0.8 mL/min. The scanning wave of diode array detector is 200-400 nm.

Thin layer chromatographic (TLC) analysis is performed on silica gel GF254 of Sanpont-group. Speckles are detected with UV light generally and in some cases other processes may also be used. In these cases, the thin layer plate is spread with iodine (about 1 g iodine is added into 10 g silica gel with complete mixing), vanillin aldehyde (about 1 g vanillin aldehyde is dissolved in 100 mL 10% $H_2SO_4$), ninhydrin (available from Aldrich) or particular developer (($NH_4$)$_6$ $Mo_7O_{24}$.4$H_2O$, 5 g ($NH_4$)$_2$Ce(IV)($NO_3$)$_6$, 450 mL $H_2O$ and 50 mL concentrated $H_2SO_4$ are completely mixed) and the compound is detected. With a process similar as that described in Still, W. C.; Kahn, M.; and Mitra, M. Journal of Organic Chemistry, 1978, 43, 2923-2925, the flash column chromatography is performed on 40-63 μm (230-400 mesh) silica gel from Silicycle. Common solvents in flash column chromatography or thin layer chromatography comprise dichloromethane/methanol, ethyl acetate/methanol and hexane/ethyl acetate mixture.

Preparative chromatographic analysis is performed on Gilson-281 Prep LC 322 system with Gilson UV/VIS-156 detector, and the chromatographic column is Agella Venusil ASB Prep C18, 5 m, 150×21.2 mm; Phenomenex Gemini C18, 5 m, 150×30 mm; Boston Symmetrix C18, 5 m, 150×30 mm; or Phenomenex Synergi C18, 4 m, 150×30 mm. Low gradient acetonitrile/water is used to elute the compound when the velocity is about 25 mL/min, wherein the water contains 0.05% HCl, 0.25% HCOOH or 0.5% $NH_3.H_2O$, and the total operational time is 8-15 min.

The following abbreviations are used herein: n-BuLi: n-butyllithium; THF: tetrahydrofuran; SEM: 2-(trimethylsilyl)ethoxyl methyl; DIPEA: diisopropyl ethyl amine; IPA: isopropanol; TFA: trifluoroacetic acid; DMF: N,N-dimethylformamide; n-BuOH: n-butanol; $Et_3SiH$: triethylsilane.

Advantageous Effect

The compounds according to the invention have high binding activity to Toll-like receptor 7 and low binding activity to Toll-like receptor 8, showing better selectivity, activity and safety as well as lower side effect, and can be used to effectively treat and prevent viral infection, particularly hepatitis B or hepatitis C viral infection.

EXAMPLES

The following Examples are provided for a person skilled in the art to clearly illustrate and practice the invention. They are illustrative and exemplary only and should not be understood as a limitation to the scope. Unless stated otherwise, the ratios (including percentages) or parts are based on weight.

Example 1

2-butoxy-7-((2-(pyrrolidin-1-ylmethyl)thiazol-5-yl)methyl)-5H-pyrrolo[3,2-d]pyrimidin-4-amine (I)

To a 500 mL reaction bottle were added thiazol-2-formaldehyde (25.00 g, 220.90 mmol) and tetrahydrofuran (300.0 mL), which was stirred for 5 min and then glacial acetic acid (39.80 g, 662.90 mmol) was added. The system was cooled to 0-10° C. with stirring and pyrrolidine (13.80 g, 194.40 mmol) was added dropwise. The temperature was kept below 10° C. during addition. After addition, sodium triacetoxyborohydride (56.20 g, 265.10 mmol) was added in portions. The reaction was performed at 10-20° C. for 12 hr and was monitored with TLC until the starting materials totally disappeared. After completion of the reaction, to the reaction liquid was added aqueous saturated sodium bicarbonate slowly to pH of 9-10 and the reaction liquid was extracted with 150 mL of ethyl acetate three times. The organic phases were combined, dried over anhydrous sodium sulfate and concentrated under reduce pressure. The residue was purified with column chromatography (mobile phase gradient: ethyl acetate/petroleum ether: 3/1/–1/1) to give 15.00 g of title compound as yellow oil, yield: 40.3%.

$^1$H NMR (400 MHz, CHLOROFORM-d) δ 7.71 (d, J=3.26 Hz, 1H), 7.26-7.32 (m, 1H), 4.02 (s, 2H), 2.60-2.75 (m, 4H), 1.84 (td, J=3.20, 6.65 Hz, 4H).

Step 2: 2-(pyrrolidin-1-ylmethyl)thiazol-5-formaldehyde

To a 500 mL three neck flask were added 2-(pyrrolidin-1-ylmethyl)thiazole (15.00 g, 89.10 mmol) and tetrahydrofuran (250.00 mL), which was cooled to −78° C. with dry ice acetone. At −78° C. n-butyllithium (2.5 M, 71.3 mL) was slowly added dropwise. After addition, the reaction mixture was stirred for 30 min at −78° C. At −78° C., to the reaction liquid was added DMF (13.00 g, 178.30 mmol) dropwise. After addition, the reaction mixture was further stirred at −78° C. for 30 min. The completion of reaction was detected with TLC. The reaction liquid was quenched with 50 mL of saturated aqueous ammonium chloride and extracted with 150 mL of ethyl acetate. The combined organic phases were dried over saturated sodium sulfate, filtered and concentrated under reduced pressure to give 15.00 g of title compound as yellow oil and the crude was used for the next step directly.

$^1$H NMR (400 MHz, CHLOROFORM-d) δ 10.03 (s, 1H), 8.32 (s, 1H), 4.03 (s, 2H), 2.73 (t, J=6.02 Hz, 4H), 1.86 (td, J=3.20, 6.65 Hz, 4H).

Step 3: 2,4-dichloro-5-((2-(trimethylsilyl)ethoxyl)methyl)-5H-pyrrolo[3,2-d]pyrimidine 2,4-dichloro-5H-pyrrolo[3,2-d]pyrimidine (4.00 kg, 21.28 mol) was dissolved in DMF (20.00 L); at room temperature (25° C.) DIPEA (2.58 kg, 20.00 mol) was added in portions and the reaction mixture was stirred for 30 min subsequently. The reaction liquid was cooled to 0° C. with ice bath and then SEM-Cl (4.00 kg, 24.00 mol) was slowly added dropwise at a rate of 1-2 drop/second over 5 hours. After addition, the reaction liquid was stirred for 4 hour at 0° C. Completion of the reaction was monitored with HPLC. The reaction liquid was quenched with 70 L of water and extracted with ethyl acetate (15L×3) after dilution. The combined organic phases were washed with 1M aqueous hydrochloric acid (5L×2) and saturated saline solution (7 L×2) successively, and the solvent was distilled off under reduced pressure to give the title compound (6.40 kg, 20.11 mol, yield 94.50%).

$^1$H NMR (400 MHz, DMSO-d$_6$) δ 8.24-8.35 (m, 1H), 6.70-6.85 (m, 1H), 5.77 (s, 2H), 3.45-3.57 (m, 2H), 0.74-0.86 (m, 2H), 0.00 (s, 9H).

Step 4: 2-chloro-5-((2-(trimethylsilyl)ethoxyl)methyl)-5H-pyrrolo[3,2-d]pyrimidin-4-amine In a 10 L autoclave, 2,4-dichloro-5-((2-(trimethylsilyl)ethoxyl)methyl)-5H-pyrrolo[3,2-d]pyrimidine (1.60 kg, 5.03 mol) was dissolved in isopropanol (1.60 L) and aqueous ammonia (4 L) was added in one portion at room temperature (25° C.). The reaction mixture was stirred at 95° C. for 7 hours and the completion of reaction was monitored with HPLC. The reaction liquid was cooled to room temperature spontaneously and filtration with buchner funnel to give black brown solid. The solid was slurried with ethyl acetate/n-heptane (1/1, 5 L×2), slurried with ethyl acetate (4 L) successively to give the title compound as brown solid (1.25 kg, 4.18 mol, yield 83.1%).

$^1$H NMR (400 MHz, DMSO-d$_6$) δ 7.61-7.77 (m, 1H), 6.97-7.19 (m, 2H), 6.28-6.38 (m, 1H), 5.54-5.67 (m, 2H), 3.43-3.53 (m, 2H), 0.76-0.91 (m, 2H), 0.07 (s, 9H).

Step 5: 2-butoxy-5-((2-(trimethylsilyl)ethoxyl)methyl)-5H-pyrrolo[3,2-d]pyrimidin-4-amine Under the protection of nitrogen, to n-BuOH (17.0 L) was slowly added metal sodium (525.05 g, 22.84 mol) in portions. After addition, the system was warmed to 60° C. and continued to be stirred at that temperature until the complete dissolution of metal sodium. Then the system was cooled to 25° C. and 2-chloro-5-((2-(trimethylsilyl)ethoxyl)methyl)-5H-pyrrolo[3,2-d]pyrimidin-4-amine (1.95 kg, 6.53 mol) was added in portions. After uniform mixing with stirring, the reactants were stirred for 8 hours at 90° C. and completion of the reaction was monitored with HPLC. The reaction mixture was cooled to 25° C. spontaneously and then poured slowly into 30 L of aqueous ammonium chloride and extracted with ethyl acetate (15 L×3). The combined organic phases were washed with saturated saline solution (20 L×2), dried over anhydrous Na$_2$SO$_4$, and filtered. After distillation of solvent under reduced pressure, the residue was slurried in n-heptane (4 L). Filtration was performed to give solid, which was slurried in ethyl acetate (5 L) to give the title compound as yellowish white solid (1.53 kg, 4.55 mol, 69.7%).

$^1$H NMR (400 MHz, DMSO-d$_6$) δ 7.49-7.54 (m, 1H), 6.54-6.62 (m, 2H), 6.15-6.20 (m, 1H), 5.54 (s, 2H), 4.10-4.22 (m, 2H), 3.42-3.55 (m, 2H), 1.58-1.73 (m, 2H), 1.35-1.47 (m, 2H), 0.90-0.96 (m, 3H), 0.83-0.89 (m, 2H), 0.05 (s, 9H).

Step 6: 2-butoxy-5H-pyrrolo[3,2-d]pyrimidin-4-amine

2-butoxy-5-((2-(trimethylsilyl)ethoxyl)methyl)-5H-pyrrolo[3,2-d]pyrimidin-4-amine (1.10 kg, 3.27 mol) was dissolved in TFA (5.50 L) and the reaction liquid was stirred for 16 hours at 25° C. Completion of the reaction was monitored with HPLC and TFA was distilled off under reduced pressure. The residue was dissolved in methanol (1.2 L) and ice water (1.2 L) and pH of the system was adjusted to 12 with concentrated aqueous ammonia with uniform stirring and then stirred for 2 hours. Precipitate continued to appear in the solution. After filtration, the filter cake as white solid was slurried with 15% aqueous ammonia (1.2 L×3) and ethyl acetate (4 L) to give the title compound as white solid (550.00 g, 2.67 mol, 81.7%).

$^1$H NMR (400 MHz, METHANOL-d$_4$) δ 7.37 (d, J=2.89 Hz, 1H), 6.29 (d, J=3.01 Hz, 1H), 4.27 (t, J=6.53 Hz, 2H), 1.75 (d, J=7.91 Hz, 2H), 1.44-1.61 (m, 2H), 1.00 (t, J=7.40 Hz, 3H).

Step 7

(4-amino-2-butoxy-5H-pyrrolo[3,2-d]pyrimidin-7-yl)-[2-(pyrrolidin-1-ylmethyl)thiazol-5-yl]methanol

((4-amino-2-butoxy-5H-pyrrolo[3,2-d]pyrimidin-7-yl)-hydroxylmethyl)-[2-(pyrrolidin-1-methylene)thiazol-5-yl]methanol To a 500 mL three neck flask were added 2-butoxy-5H-pyrrolo[3,2-d]pyrimidin-4-amine (10.00 g, 48.49 mmol), potassium carbonate (7.37 g, 53.34 mmol), water (100 mL) and isopropanol (100 mL), to which was added 2-(pyrrolidin-1-ylmethyl)thiazol-5-formaldehyde (14.27 g, 72.74 mmol) with stirring. The reaction was performed at 25° C. for 16 hr and 2-(pyrrolidin-1-ylmethyl)thiazol-5-formaldehyde was monitored with LCMS for completion of the reaction. The reaction liquid was added with 100 mL of water for dilution and extracted with 100 mL of dichloromethane three times. The combined organic phases were dried over anhydrous sodium sulfate, filtered off solid and concentrated under reduced pressure to give residue, which was purified with column chromatography (mobile phase gradient: dichloromethane/methanol/aqueous ammonia/: 30/1/0.1 to 10/1/0.1) to give the title compound as brown solid (5.20 g, 12.92 mmol, yield: 26.6%). MS (ESI) m/z: 403.3 [M+H$^+$].

Step 8

2-butoxy-7-((2-(pyrrolidin-1-ylmethyl)thiazol-5-yl)methyl)-5H-pyrrolo[3,2-d]pyrimidin-4-amine To a 100 mL eggplant flask were charged (4-amino-2-butoxy-5H-pyrrolo[3,2-d]pyrimidin-7-yl)-[2-(pyrrolidin-1-ylmethyl)thiazol-5-yl]methanol (5.10 g, 12.60 mmol), triethylsilane (10.00 mL) and trifluoroacetic acid (40.00 mL) and the reaction mixture was stirred at 20° C. for 12 hours. The raw materials were monitored with LCMS for completion of the reaction. The solvent was removed by concentration under reduced pressure. To the system was added 100 mL of ethyl acetate and then saturated sodium carbonate solution was added to adjust the solution to pH=9-10. Extraction was performed with 50 mL of ethyl acetate three times. The organic phases were combined, dried over anhydrous sodium sulfate, filtered off solid and concentrated under reduced pressure to give residue, which was separated with prep. High Performance Liquid Chromatography to give 4.2 g of 2-butoxy-7-((2-(pyrrolidin-1-ylmethyl)thiazol-5-yl)methyl)-5H-pyrrolo[3,2-d]pyrimidin-4-amine as light yellow oil (diformate of the title compound).

$^1$HNMR (400 MHz, Methanol-$d_4$) δ 8.30 (s, 2H), 7.61 (s, 1H), 7.41 (s, 1H), 4.51 (s, 2H), 4.44 (q, J=6.6 Hz, 2H), 4.24 (s, 2H), 3.33-3.28 (m, 4H), 2.02 (s, 4H), 1.83-1.73 (m, 2H), 1.56-1.46 (m, 2H), 0.99 (t, J=7.2 Hz, 3H).

Experimental Example 1: Toll-Like Receptor 7 and Toll-Like Receptor 8 In Vitro Receptor Binding Activity Reagents:

HEK-blue hTLR7 cell and HEK-blue hTLR8 cell (available from InvivoGen)

DMEM medium heat inactivated fetal bovine serum

Anti Mycoplasma reagent Normocin™ bleomycin blasticidin

The GS-9620 and R848 used have the following structures. GS-9620 can be prepared according the process disclosed in US20100143301; R848 is purchased from ABGENT (Catalog: IMG-2208, 0.5 mg).

GS9620

R848/Resiquimod

Scheme:

1. Preparation of 96-well compound plate:

The compounds were gradient diluted with DMSO in 3-fold using liquid work station POD starting at a concentration of 10 mmol/L and 10 points were diluted (2nd column to 11th column, and each point was duplicated). At 12th column, 1 μL of 5 mg/mL positive compound R848 was added as positive control; and at 1 st column, 1 μL of DMSO was added as negative control. Each well contained 1 μL of DMSO.

2. The cells in cell culture flask were collected and the cell density was diluted to 250,000 cells/mL.

3. 200 μL (50,000 cells/well) of cell suspension was added into prepared compound plate and the final concentration of DMSO in each well was 0.5%.

4. The culture plates containing cells and the compounds were incubated in $CO_2$ incubator for 24 h at 37° C., 5% $CO_2$.

5. After 24 h incubation, 20 μL of supernatant was removed from each well of the cell culture plates to a 96-well transparent assay plate. To each well of the assay plate was added 180 μL of Quanti-Blue reagent and the plate was incubated in an incubator at 37° C., 5% $CO_2$ for 1 h.

6. After 1 h, the content of alkaline phosphatase in 20 μL of supernatant was determined using Microplate Reader at $OD_{650}$.

7. $EC_{50}$ of each compound was obtained with Prism software.

Results were shown in Table 1:

TABLE 1

| Test sample | TLR7 $EC_{50}$ (nM) | TLR8 $EC_{50}$ (nM) |
|---|---|---|
| GS-9620 | 517 | 7867 |
| Example 1 | 454.1 | 29332 |

According to the above table, the compound according to the invention showed higher in vitro receptor binding activity to Toll-like receptor 7 than the control Toll-like receptor 7 agonist GS-9620 and lower in vitro receptor binding activity to Toll-like receptor 8 than the control Toll-like receptor 7 agonist GS-9620. The compound according to the invention has significant difference in selectivity for various receptors, showing better effect than the prior art.

Experimental Example 2: Pharmacokinetics Assay in Rat 12 male SD rats were divided into 4 groups with 3 SD rats in each group. 2 groups of animals were administered by intravenous injection (IV) 1 mg/kg of the control Toll-like receptor 7 agonist GS-9620 and Example 1 compound as 10% hydroxypropyl-β-cyclodextrin aqueous solution (concentration is 0.5 mg/mL), respectively. The other 2 groups were administered orally (PO) 5 mg/kg of GS-9620 and 3 mg/kg of Example 1 compound as 0.5% methylcellulose/0.2% Tween 80 pure water suspension (concentration is 1 mg/mL). Each rat with intravenous injection was collected for whole blood samples which were prepared into plasma 2, 15, 30 min and 1, 2, 4, 8, 24 h continuously after administration. Each rat with oral administration was collected for whole blood samples which were prepared into plasma 15, 30 min and 1, 2, 4, 8, 24 h continuously after administration. The plasma concentrations of GS-9620 and Example 1 compound were determined with LC-MS/MS.

The results were shown in Table 2.

TABLE 2

Mean plasma drug concentration

| | Compound name | | | |
|---|---|---|---|---|
| | GS-9620 | | Example 1 | |
| Time (h) | IV1 (1 mpk) | PO1 (5 mpk) | IV2 (1 mpk) | PO2 (3 mpk) |
| 0.083 | 170 | — | 500 | — |
| 0.25 | 102 | 56.3 | 277 | 45.4 |
| 0.5 | 65.4 | 33.2 | 197 | 52.0 |
| 1 | 48.1 | 83.4 | 120 | 86.8 |
| 2 | 21.6 | 136 | 66.1 | 113 |
| 4 | 13 | 16.7 | 30.6 | 23.6 |
| 8 | 4.17 | 9.49 | 13.1 | 5.64 |
| 24 | ND | ND | ND | ND |
| C0 or Cmax (nM) | 220 | 164 | 673 | 148 |
| T½ (hr) | 2.57 | 2.24 | 3.08 | 1.54 |
| Vdss (L/kg) | 32.8 | — | 13.5 | — |
| Cl (mL/min/kg) | 205 | — | 75.8 | — |
| AUC0-last (nM · hr) | 185 | 316 | 541 | 313 |
| AUC0-inf (nM · hr) | 201 | 359 | 573 | 325 |

Administration groups: group 1: vehicle, 10% HP-β-CD; group 2: GS-9620, 20 mg/kg; groups 3: Example 1 compound, 20 mg/kg Blood collection: since day 3 after 1$^{st}$ administration, twice per week, 8 weeks in total;

Liver collection: liver sample was collected on day 64 after 1$^{st}$ administration.

The details were shown in Table 3 and Table 4.

TABLE 3

| | Injection procedure | | |
|---|---|---|---|
| Mouse number | AAV-HBV v.g./200 µL | Injection means | Blood collection |
| 30 + 6 | 1 * 10$^{11}$ | 200 µL/animal, caudal vein, from day 0 | 1. On day 14 and day 21 after virus injection, 30 mice were divided into 6 groups, according to HBV DNA, HBsAg and HBeAg blood level; 2. Blood was collected on day 26 of virus injection as prepared sample for administration. |

*HBsAg: hepatitis B surface antigen; HBeAg: hepatitis B E antigen

TABLE 4

| | | | Experimental procedure | | | | |
|---|---|---|---|---|---|---|---|
| Group | Mouse number | Compound | Administration amount (mg/kg) | Administration volume (mL/kg) | Administration means | Blood collection time | Liver collection time |
| 1 | 5 | Vehicle | / | 10 | After day 26 of virus injection, intragastric administration was performed, once every three days, 6 weeks in total. | The first blood collection was performed on day 3 after administration, twice per week, 8 weeks in total. | Day 64 after 1$^{st}$ administration. |
| 2 | 5 | GS9620 | 20 | | | | |
| 3 | 5 | Example 1 | 20 | | | | |

Under the equivalent conditions, as for both the intravenous injection and oral administration (converted administration amount), compared to control Toll-like receptor 7 agonist GS-9620, the compound according to the invention showed higher exposure in rats.

Experimental Example 3: In Vivo Pharmacodynamics Assay in Mouse Model Infected with AAV (Adeno Associated Virus)-Carrying Hepatitis B Virus (HBV)

Figure 1:
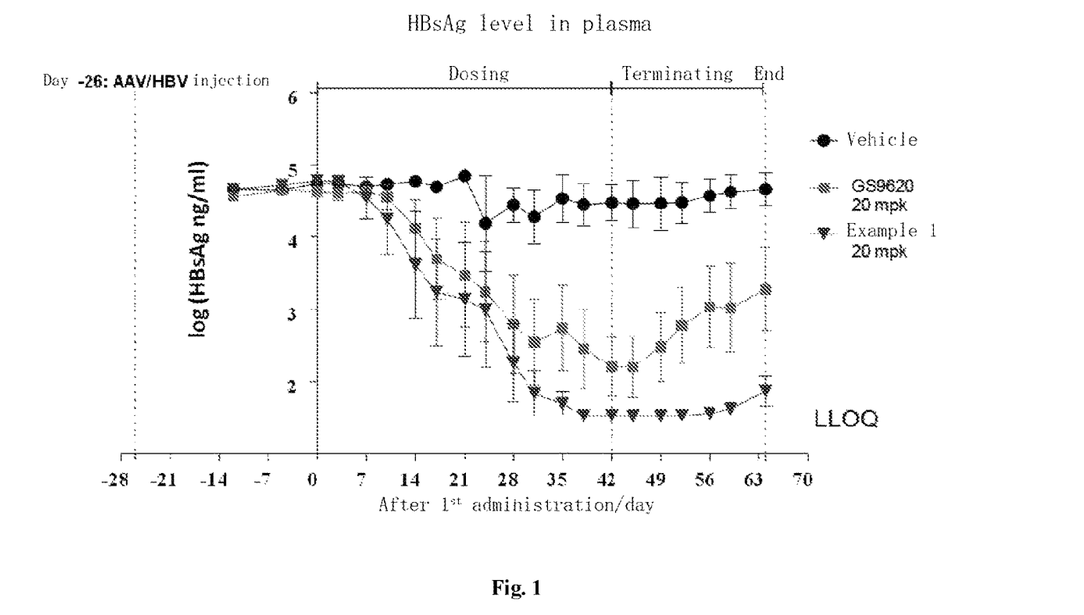
FIG. 1: In vivo results of pharmacodynamics test in mouse model infected with AAV-carrying hepatitis B virus (plasma HBsAg copy level).
Figure 2:
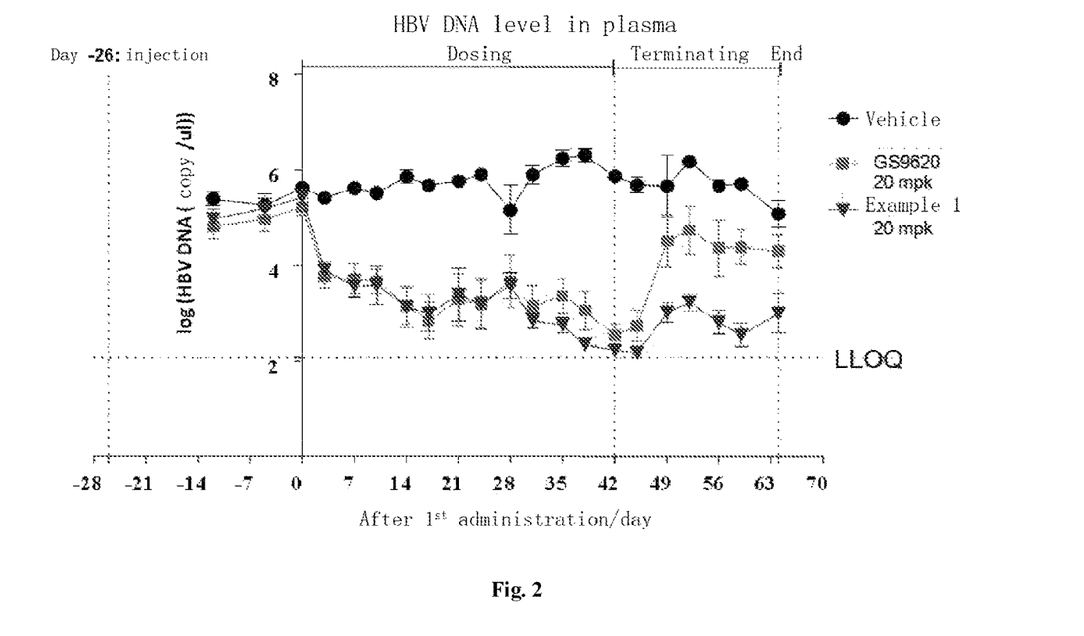
FIG. 2: In vivo results of pharmacodynamics test in mouse model infected with AAV-carrying hepatitis B virus (plasma HBV DNA copy level).
Figure 3:
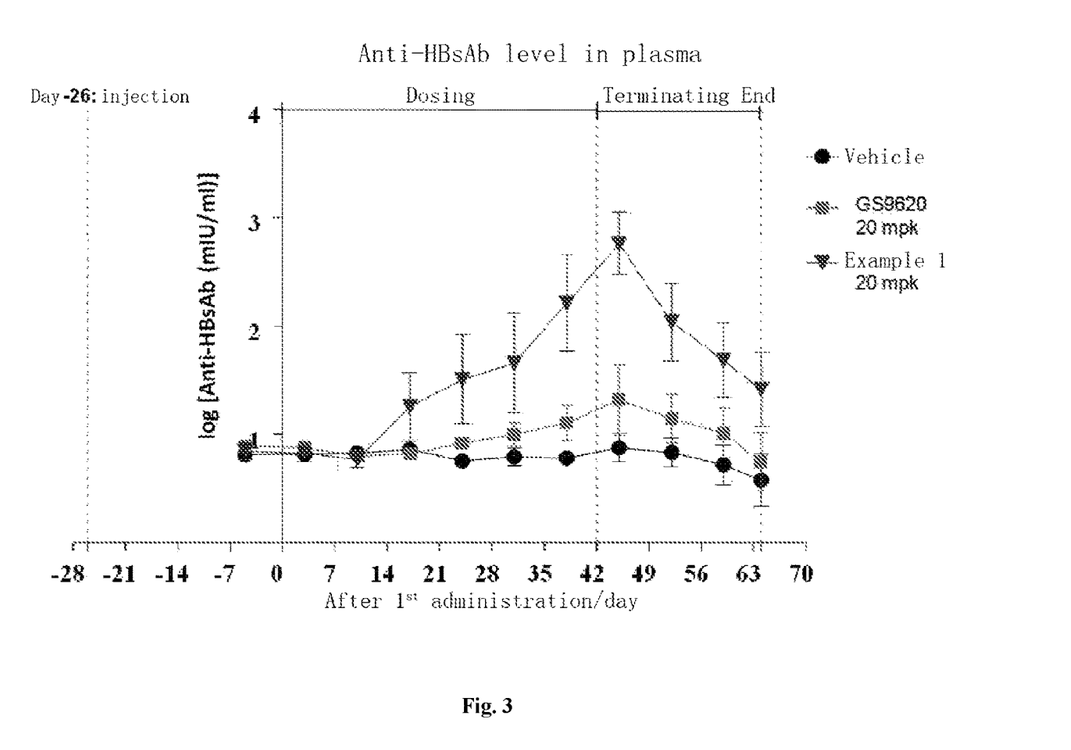
FIG. 3: In vivo results of pharmacodynamics test in mouse model infected with AAV-carrying hepatitis B virus (plasma Anti-HBsAb producing level).

Experimental design and procedures:
Administration route: intragastric administration
Administration time: since day 26 after virus injection, one administration every three days, 6 weeks in total The detailed results of in vivo pharmacodynamics assay in mouse model infected with AAV-carrying hepatitis B virus were shown in FIGS. 1-3. Data of HBV DNA copy number in plasma, HBsAg copy number in plasma and Anti-HBsAb (hepatitis B surface antigen antibody) producing level showed, Example 1 compound has better efficacy than control Toll-like receptor 7 agonist GS-9620 under equivalent conditions, showing more advantageous effect.

Unless otherwise indicated, all numbers expressing quantities of ingredients, cell culture, treatment conditions, and so forth used in the specification, including claims, are to be understood as being modified in all instances by the term "about". Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. A person skilled in the art will recognize, or be able to ascertain using no more than routine experimentation, many equivalents to the specific embodiments of the invention described herein. Such equivalents are intended to be encompassed by the appended claims.

Many modifications and variations of the invention can be made without departing from its spirit and scope, as will be apparent to a person skilled in the art. The specific embodiments described herein are offered by way of example only and are not meant to be limiting in any way. It is intended that the specification and examples be considered as exemplary only, with a true scope and spirit of the invention being indicated by the appended claims.

The invention claimed is:

1. A compound of formula (I) or a pharmaceutically acceptable salt thereof, (I)

wherein
R$_1$ and R$_2$ together with the N atom to which they are attached form a 4-8 membered heterocycloalkyl; wherein the 4-8 membered heterocycloalkyl is optionally substituted with one or more R$_3$; and R$_3$ is independently at each occurrence selected from the group consisting of hydroxyl, halogen, cyano, C$_{1-4}$alkyl and C$_{1-4}$alkoxy.

2. The compound according to claim 1 or the pharmaceutically acceptable salt thereof, wherein
the 4-8 membered heterocycloalkyl contains 0, 1, 2 or 3 additional heteroatoms selected from the group consisting of N, O and S.

3. The compound according to claim 2 or the pharmaceutically acceptable salt thereof, wherein
the 4-8 membered heterocycloalkyl is 4 membered, 5 membered, 6 membered, 7 membered or 8 membered heterocycloalkyl.

4. The compound according to claim 1 or the pharmaceutically acceptable salt thereof, wherein
R$_3$ is independently at each occurrence selected from the group consisting of hydroxyl, F, Cl, Br, CN, methyl, ethyl, propyl, methoxyl, ethoxyl and propoxy.

5. The compound according to claim 1 or the pharmaceutically acceptable salt thereof, wherein
the group formed by R$_1$, R$_2$ together with the N atom to which they are attached is selected from the group consisting of:

6. The compound according to claim 5 or the pharmaceutically acceptable salt thereof, wherein
the group formed by R$_1$, R$_2$ together with the N atom to which they are attached is 7. The compound according to claim 1 or the pharmaceutically acceptable salt thereof, wherein the compound has the following formula:

8. A pharmaceutical composition, comprising the compound according to claim 1 and/or the pharmaceutically acceptable salt thereof in therapeutically or prophylactically effective amount, and one or more pharmaceutically acceptable carriers and/or excipients.

9. A method for treating hepatitis B viral infection or hepatitis C viral infection, comprising administrating to a subject in need thereof the compound according to claim 1 or the pharmaceutically acceptable salt thereof.

10. A method for treating hepatitis B viral infection or hepatitis C viral infection, comprising administrating to a subject in need thereof the compound according to claim 7 or the pharmaceutically acceptable salt thereof.

11. A method for treating hepatitis B viral infection or hepatitis C viral infection, comprising administrating to a subject in need thereof the pharmaceutical composition according to claim 8.

* * * * *